United States Patent
Snyder, Jr.

[11] Patent Number: 5,902,335
[45] Date of Patent: May 11, 1999

[54] MULTIPLE SECTION BREAST PROSTHESIS

[75] Inventor: John E. Snyder, Jr., Waco, Tex.

[73] Assignee: Capital Marketing Technologies, Inc., Waco, Tex.

[21] Appl. No.: 08/940,403

[22] Filed: Oct. 1, 1997

[51] Int. Cl.⁶ .................................................. A61F 2/52
[52] U.S. Cl. .................................................. 623/7
[58] Field of Search ............................... 623/7, 8

[56] References Cited

U.S. PATENT DOCUMENTS

| | | | |
|---|---|---|---|
| 2,543,499 | 4/1951 | Kausch | 2/267 |
| 3,619,819 | 11/1971 | Mann | 623/7 |
| 3,663,968 | 5/1972 | Mohl et al. | 3/36 |
| 3,811,133 | 5/1974 | Harris | 3/36 |
| 3,858,248 | 1/1975 | Crowe | 3/36 |
| 3,896,506 | 7/1975 | Hankin et al. | 3/36 |
| 3,986,213 | 10/1976 | Lynch | 623/8 |
| 4,019,209 | 4/1977 | Spence | 3/36 |
| 4,086,666 | 5/1978 | Vaskys et al. | 3/36 |
| 4,125,117 | 11/1978 | Lee | 128/481 |
| 4,195,639 | 4/1980 | Lee | 128/481 |
| 4,364,880 | 12/1982 | Howse | 264/28 |
| 4,380,569 | 4/1983 | Shaw | 428/283 |
| 4,401,492 | 8/1983 | Pfrommer | 156/61 |
| 4,426,742 | 1/1984 | Prahl | 3/36 |
| 4,428,082 | 1/1984 | Naficy | 623/8 |
| 4,605,412 | 8/1986 | LaForest et al. | 623/8 |
| 4,650,487 | 3/1987 | Chaglassian | 623/8 |
| 4,671,255 | 6/1987 | Dubrul et al. | 128/1 |
| 4,676,795 | 6/1987 | Grundei | 623/8 |
| 4,681,587 | 7/1987 | Eberl et al. | 623/7 |
| 4,701,230 | 10/1987 | Loi | 156/145 |
| 4,790,848 | 12/1988 | Cronin | 623/8 |
| 4,826,501 | 5/1989 | Grundei | 623/8 |
| 4,950,291 | 8/1990 | Mulligan | 623/8 |
| 5,035,758 | 7/1991 | Degler et al. | 156/61 |
| 5,171,321 | 12/1992 | Davis | 623/7 |
| 5,370,688 | 12/1994 | Schulz et al. | 623/7 |
| 5,534,023 | 7/1996 | Henley | 623/8 |
| 5,549,671 | 8/1996 | Waybright et al. | 623/8 |

FOREIGN PATENT DOCUMENTS

| | | |
|---|---|---|
| 0005275 | 5/1979 | European Pat. Off. . |
| 2 410 472 | 8/1979 | France ................. 623/7 |
| 2121291 | 5/1983 | United Kingdom . |

Primary Examiner—Michael J. Milano
Assistant Examiner—Tram A. Nguyen
Attorney, Agent, or Firm—Sidley & Austin

[57] ABSTRACT

A lightweight breast prosthesis having a first section and a second section. The first section having a gel-like consistency simulating the human breast and the second section containing a density-reducing agent to provide a lightweight prosthesis which provides excellent mimicking of the human breast form.

9 Claims, 1 Drawing Sheet

MULTIPLE SECTION BREAST PROSTHESIS

TECHNICAL FIELD OF THE INVENTION

The present invention relates to a prosthesis and in particular, a breast prosthesis having dual sections which permit reduction in weight of the prosthesis while maintaining a prosthesis which mimics the movements of the human breast.

BACKGROUND OF THE INVENTION

There have been many attempts to produce a breast prosthesis for use by mastectomy patients. Such prosthesis are generally considered important to the psychological health of the patient. However, in order to be of benefit, a prosthesis must mimic the human breast sufficiently such that the wearer believes that the presence of the prosthesis will be undetected by those the wearer meets. In addition to the movement and appearance of the prosthesis, it must also be easy to use and comfortable to wear.

While prosthetic devices may be implanted, external prostheses have achieved widespread acceptance because they do not require additional surgery, avoid the risks and health hazards of implants, are easily changed such that the user may enjoy improvements in the technology, and are easy to use.

Early prosthetic devices utilized many different materials. Silicone gel became widely accepted for use in prosthesis because of its resilient properties. At one time in the art, silicone prosthesis were prepared having a weight comparable to the weight of a human breast. It was believed that this was advantageous because in the event that the user had one natural breast and one prosthetic breast, that the balancing of the weight would be important. However, it was determined that matching the weight resulted in user discomfort. In U.S. Pat. No. 4,380,569, the use of microspheres mixed into the silicone gel to reduce weight is disclosed for the manufacturer of a prosthesis. While this method achieved weight reduction, the introduction of glass spheres, the bonding of the spheres with the silicone gel, created a stiff product which did not mimic the human breast as well as silicone gel alone.

Thus, there has been a continued need for a prosthetic device which mimics the movements of a human breast, which is lightweight and comfortable to wear. The present invention has advantages of achieving reduction in weight to improve comfort for the patient while not sacrificing movement, feel and texture qualities of the prosthesis.

SUMMARY OF THE INVENTION

The invention is a lightweight breast prosthesis which provides excellent mimicking of the human breast while achieving a reduction in weight of the prosthesis. The prosthesis has a first outer section extending from the back of the prosthesis and being disposed over an inner section. The inner section extends from the back to the inside surface of the outer section. The outer section is comprised of a gel which has a consistency and feel similar to the human breast. The inner section utilizes a similar gel incorporating a density reducing agent to achieve predetermined reduced weight. The consistency of the outer and inner section can be varied as desired to achieve the desired balance between the characteristics of touch and feel of the total prosthesis, look of the total prosthesis and weight of the total prosthesis. The consistency of each section can vary as the dimensions of the sections vary. For example, if the volume of one section is much larger than that of the other section, wider variations in consistency of the two sections typically can be employed.

In the preferred embodiment, the outer section and the inner section are held within two flexible bags. The bags are preferably made from polyurethane and incorporate a portion of the back of the prosthesis as part of the bag. The outer section bag contains the gel of the outer layer and the inner section bag contains a mixture of the gel and density reducing agent. The prosthesis is formed by taking a back sheet of polyurethane and attaching a polyurethane sheet of predetermined shape to form the bag to contain the inner section. An outer polyurethane sheet is attached to the back sheet such that the seam formed from the back sheet and the outer sheet is spaced apart from and outside of the seam formed from by the back sheet and inner sheet.

Density reducing agent means a substance which has a density less than the density of the silicone gel used in the prosthesis, and which is in a form capable of distribution in small discrete portions. The density reducing material may be entrapped air or gas bubbles, expanded perlite, styrofoam beads, glass microballoons or plastic microballoons.

The inner section of the prosthesis incorporates sufficient density reducing material to reduce the density of the inner section from 5 to 35% of the density the inner section would have if made entirely from silicone gel. The volume of the inner section is preferably from about 20 to about 72% of the volume of the prosthesis. In the preferred embodiment, sufficient density reducing agent is added to reduce the weight of the total prosthesis from 2.5 to 25%.

In the preferred embodiment, the prosthesis is formed from having a backing made of the flexible film and having attached to one side an inner sheet the combination of the backing and inner sheet defining a volume for retaining the inner section of the prosthesis. Disposed on the back sheet is an outer sheet disposed over the inner sheet which together with the backing and the inner sheet defines the volume for said outer section. The prosthesis includes an outer section of solely silicone gel having a consistency like that of a natural breast and an inner section made of silicone gel which contains a density reducing agent.

In preferred embodiments of the invention, the outer section encircles the back of the inner section. The width of the outer section at its thinness portion is preferably about 0.5 inches more which has been found sufficient to provide a natural feel to the prosthesis.

The invention preferably contains the same type of silicone gel in both sections and contains glass microspheres as a density reducing agent in the inner section.

BRIEF DESCRIPTION OF THE DRAWINGS

Embodiments of the invention will be described in reference to one or more of the following drawings in which.

DETAILED DESCRIPTION

Figure 1:
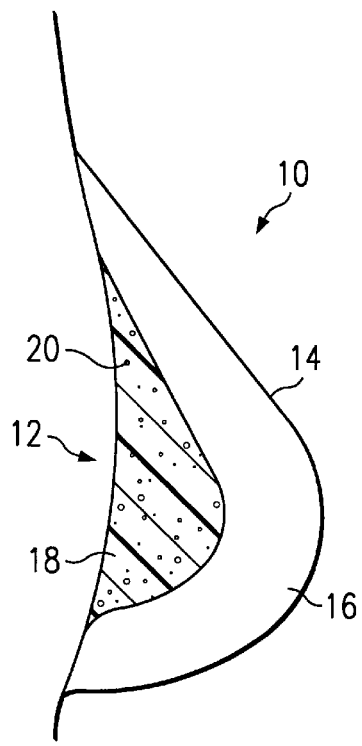
FIG. 1 is a cross-sectional area of the first embodiment of the present invention.

The invention will now be described with reference to preferred embodiments and such description is not considered limiting of the invention. In the drawings, like numbers refer to like items. Referring now to FIG. 1, there is illustrated a breast prosthesis 10 in a cross-section. The prosthesis 10 has a back side 12 and an outer surface 14. Outer surface 14 is in a shape resembling a human breast. Back 12 is shaped such that it may lay against the patient's chest. The prosthesis has two sections, an outer section 16 which extends from a portion of back 12 and ends at outer surface 14. Outer section 16 covers inner section 18. Outer section 16 is roughly in the shape of a cone. Inner section 18 is made of a gel material in which a density reducing agent, such as glass microballoons 20, have been entrapped. Outer section 16 and inner section 18 can be adhered, affixed together, or molded to each other. The inner section 18 has a volume which is from about 20 to 72% of the volume of the entire prosthesis 10.

The composition of the prosthesis 10 is preferably of a gel-like material which is nontoxic and has properties which allow the formed prosthesis 10 to mimic natural breasts. The preferred material for producing outer section 16 is silicone gel. Outer section 16 is formed entirely from a silicone gel. Various types of silicone gel are well known for use in breast prosthetics devices and any of these gels is suitable in the present invention. The gel may be purchased as a two-resin component system, one component of the silicone gel containing the cross-lining and is normally referred to in the trade as "silicone B" and the other silicone resin component contains a catalyst to initiate cross-linking (usually called "silicone A"). When the silicone "A" and "B" resins are mixed together and heated, a reaction involving the silicone, cross-linking agent, and catalyst result in the cross-linking and setting up of the silicone gel. As is known in the art, the stiffness of the resulting gel depends in large part upon the amount of cross-linker. Thus, the degree of cross-linking can be varied to achieve the desired feel.

The inner section 18 is preferably made of a silicone gel having glass microballoons 20 entrained therein as the density reducing agent. The microballoons are preferably the type which do not interfere with the cross-linking reaction of the gel components. Most preferably, the microballoons are glass microspheres having a diameter of less than about 150 microns. Plastic microspheres are less desired because they are not as durable and many can break during the mixing of microspheres with the uncured gel. It has also been found that preferably the amount of microballoons used in inner section 18 is a quantity which results in a reduction in weight of the inner section 18 of about 35% or less from that if no density reducing were used. The specific quantity of microballoons needed to achieve this weight reduction depends on many characteristics of the microballoons. The microballoons should be of a small particle size such that they can be easily distributed throughout the entire inner section 18 and preferably are uniformly distributed throughout the section. Small diameter microballoons are advantageous in that they are more easily dispersed within the gel in a uniform manner. A uniform distribution of small diameter microballoons produces an inner section which has more uniform consistency than a section which would have one or two large voids to reduce weight. It has been found that using a quantity of microballoons which produces a weight reduction of the inner section of more than about 35% is undesirable, as such a mixture is generally stiffer than desirable and the bonding integrity of the gel portion suffers.

Figure 2:
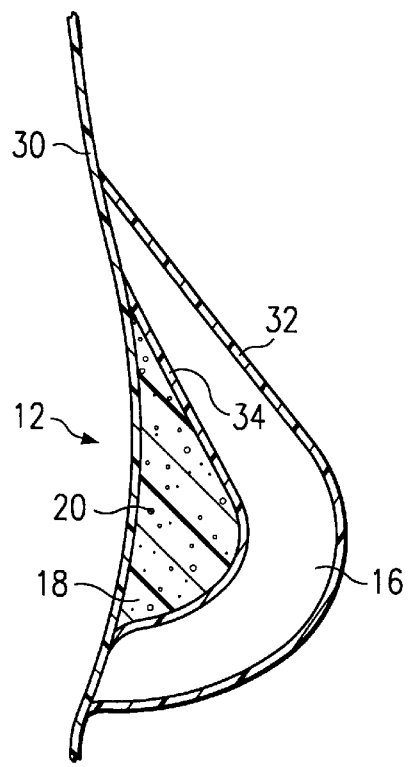
FIG. 2 is a cross-sectional area of the second embodiment of the present invention.

FIG. 2 is a cross-section of a second embodiment of the present invention. In FIG. 2, back 12 is formed by a backing sheet 30. Attached to and extending from back sheet 30 is outer sheet 32. Outer sheet 32 may be adhered to back sheet 30 in any suitable manner such as an adhesive or by welding. Thus, back sheet 30 and outer sheet 32 form an enclosure. Also extending from back sheet 30 is inner sheet 34. Inner sheet 34 is attached to back sheet 30 by any suitable mechanism. Back sheet 30 and inner sheet 34 form a second bag which is partially contained within the bag formed by sheets 30 and 32. Thus, sheets 30, 34 and 32 define the outer bag, which contains outer section 16. A portion of sheet 30 and sheet 34 form an inner bag which contains inner section 18. As illustrated in FIG. 1, outer section 16 is preferably generally in a shape resembling a cone which is disposed over inner section 18. The bonded seam of back sheet and the outer sheet is spaced apart and outside of the bonded seam formed by back sheet and the inner sheet.

Figure 3:
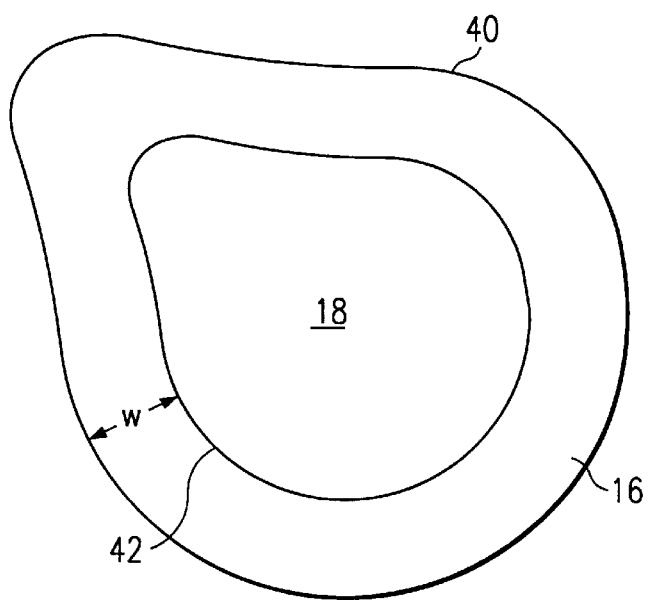
FIG. 3 is a view of the prosthesis looking at the back of the prosthesis which will be positioned against the patient's chest.

A rear view of either the prosthetic device of FIG. 1 or FIG. 2, it looks generally shown in FIG. 3. (The figures are not being drawn to scale for purposes of illustration). Outer section 16 surrounds the back of the inner section 18. Outer section 16 forms an outer rear or back perimeter 40 which surrounds the rear or back perimeter 42 of inner section 18 such that the distance between perimeter 40 and 42 i.e., width "w" can be of varying width around the prosthesis. The dimensions also vary with the size of the breast.

The outer section has a thickness which is sufficient to give the prosthesis the proper feel. Generally, it has been found that the thickness of the outer section at its thinnest point should be about 0.5 inches or more to provide a feel similar to the natural breast.

In the embodiment of FIG. 1, a prosthetic may be made by making a mold having the shape of the outer surface 14, charging the mold with sufficient silicone gel to form section 16, closing the mold with a male member in the shape of section 18. Thereafter, section 16 is cured and the male section of the mold removed. The space occupied by the male member of the mold in the shape of section 18 is then charged with a mixture of gel reactants and microspheres, the mold closed with a member having a shape to produce the desired back contour and then the gel is heated and cured. If the gel composition used for section 16 and used in section 18 are sufficiently similar, section 18 as it cures will bond to the previously cured section 16.

In the embodiment of FIG. 2, the embodiment lends to the number of methods of formation. In one method, a mold may be lined with outer sheet 32 then charged with sufficient reactants to form section 16. Then the mold then closed with a male member covered with sheet material 34. After section 16 is reacted the male member is removed and sufficient quantities to form a reactant to form section 18 are charged and reacted. Thereafter, back 30 can be adhered.

In another method, inner sheet 34 can be welded to backing sheet 30. An opening can then be made and reactive gel components sufficient to form section 18 injected into the sheet and reacted. Thereafter, sheet 32 can be welded to backing 30 and a similar process employed to form cured section 16, thereby forming an outer bag and an inner bag. Alternatively, the inner and outer bags are first formed. Access holes can then be provided to each bag, the inner bag is filled and then the outer bag can be charged with appropriate reactants to form section 18 and 16 and thereafter cured. Before the cure, the charging holes can be sealed. A method similar to that described in U.S. Pat. No. 5,370,688 entitled "Encapsulated gel breast prosthesis and method of make" assigned to the assignee of this application.

Each method has certain advantages and disadvantages with respect to the other methods to form the breast prosthesis of the present invention. The embodiment of the present invention shown in FIG. 1 has certain advantages and disadvantages with respect to the embodiment shown in FIG. 2 of the present invention. Thus, selection of the embodiment and the particular process by which to make the embodiment are subject to many subjective factors leaving the particular section to mostly a matter of one's choice.

It is preferred that in the embodiments of the present invention is that the outer section 16 and inner section 18 have substantially the same stiffness as measured by a penetrometer. A general preference is that the inner section 18 be slightly stiffer than outer section 16.

Suitable breast forms were made as exemplified in FIG. 2 of the present application in which sheets 30, 32 and 34 were polyurethane sheets. Polymeric sheet materials made from polyesters and polyethers are useful. The gel structure may be tested for appropriate consistency by a penetration test. The penetration of the gel components of the two sections may be measured using a Precision Scientific Penetrometer with a rod and foot assembly weight of 8 to 9 grams. The rod length is from 6.5 to 6.7 inches and has a diameter of 0.12 to 0.13 inches. The foot diameter is from 0.245 to 0.255 inches and the thickness is from 0.13 to 0.14 inches. The gel components are place in a Solo P3A plastic cup (3 ounce cup). The cup is filled up to about 0.75 inches from the top. This will generally result in a sample weight of about 50 grams for a sample which is entirely gel. A sample of the gel component with the density reducing agent will have a weight less than 50 grams and the weight of the sample of this component will of course depend on the amount of density reducing agent present. The sample is cured and then tested. To test the sample the rod assembly is lower to the surface of the sample so that it just touches he surface of the sample without making an indentation. The trigger on the Penetrometer is depressed and held for 10 seconds. Thereafter the amount of penetration is read. The amount of penetration should be between 5.5 mm to 7.5 mm. In a preferred embodiment the penetration of the gel component for the inner section is equal to or lesser than the penetration measured for the gel component for the outer section. Thus, preferably the inner section is as stiff or stiffer than the outer section.

The volume of the inner section is preferably about 20 to about 75% of the volume of the entire prosthesis. The weight reduction for the completed prosthesis of the invention over one made entirely from gel with no density reducing agents is from 5 to about 25%. Preferably the weight reduction of the complete prosthesis is from about 10 to 20%.

Also it is generally preferable that the microballoons be contained in a sufficient quantity such that the weight of inner section 18 is between about 5% to about 35% less than the weight of inner section 18 if it had been made solely from the gel material. The weight of the outer section of the prosthesis is from about 65% to 84% of the total weight of the prosthesis. The volumes of the inner section and the outer section can be varied as can the amount of the density reducing agent incorporated in the inner section in order to achieve the desired balance between weight reduction and feel.

While the present invention has been described with reference to preferred embodiments, it will be understood that variations and modifications can be made without departing from the scope of the invention.

What is claimed is:

1. A breast prosthesis comprising:
   (a) an outer section, said outer section comprising an outer surface shaped like a human breast and a first quantity of silicone gel, said outer surface defining a cavity filled with said first quantity of silicone gel, said first quantity of silicone gel having a first penetration value; and
   (b) an inner section adjacent said outer section, said inner section comprising a second quantity of silicone gel, said second quantity of silicone gel further comprising a density reducing agent, said second quantity of silicone gel having a second quantity weight and a second quantity volume, said density reducing present in sufficient amount so that the second quantity weight is from about 5% to about 35% less than the weight of a comparative inner section comprising silicone gel in a comparative volume of silicone gel equal in volume to said second quantity volume;
   said second quantity of silicone gel having a second penetration value less than said first penetration value, whereby sand outer section is less than said inner section in overall stiffness.

2. The prosthesis of claim 1 wherein the volume of the inner section is 20 to 75% of the volume of the prosthesis.

3. The prosthesis of claim 1 wherein said density reducing agent is glass microspheres.

4. A breast prosthesis comprising:
   (a) a back sheet of polymeric material;
   (b) an outer sheet attached to said back sheet and extending therefrom and being formable into the shape of a human breast;
   (c) an inner sheet of polymeric material welded to said back sheet at a predetermined distance inside of a welded edge of said outer sheet and backing sheet;
   (d) an outer volume defined by the connection of said outer sheet, back sheet and inner sheet wherein said outer volume is filled entirely with a first quantity of silicone gel;
   (e) an inner volume defined by the connection of said inner sheet and said backing sheet wherein said inner volume is filled with a second quantity of silicone gel containing density reducing agents distributed therethrough contained within said inner volume; and
   (f) said first quantity of silicone gel having a first penetration value and said second quantity of silicone gel having a second penetration value, said second penetration value less than said first penetration value, whereby said outer volume is less then said inner section in overall stiffness.

5. The prosthesis of claim 4 wherein said inner volume is 20 to 75% of the volume of the prosthesis.

6. The prosthesis of claim 4 wherein said density reducing agent is glass microspheres.

7. A breast prosthesis comprising:
   (a) a back sheet of polymeric material;
   (b) an outer sheet attached to said back sheet extending therefrom and being formable into the shape of a human breast;

(c) an outer volume filled with a first quantity of silicone gel;

(d) an inner volume wherein said inner volume is filled with a second quantity of silicone gel containing density reducing agents distributed therethrough contained within said inner volume; and (e) said first quantity of silicone gel having a first penetration value and said second quantity of silicone gel having a second penetration value, said second penetration value less then said first penetration value, whereby said outer volume is less than said inner section in overall stiffness (f) said prosthesis having a weight from about 2.5% to about 25% of the weight of a comparative prosthesis without density reducing agents.

8. The prosthesis of claim 7 wherein said inner volume is 20 to 75% of the volume of the prosthesis.

9. The prosthesis of claim 7 wherein said density reducing agent is glass microspheres.

* * * * *